United States Patent [19]

Baur et al.

[11] Patent Number: 5,077,039

[45] Date of Patent: Dec. 31, 1991

[54] SUBSTITUTED GLUCOSIDES

[75] Inventors: Richard Baur, Mutterstadt; Jochen Houben, Worms; Alfred Oftring, Bad Durkheim; Dieter Stoeckigt, Ludwigshaften, all of Fed. Rep. of Germany

[73] Assignee: BASF Aktiengesellschaft, Ludwigshafen, Fed. Rep. of Germany

[21] Appl. No.: 413,075

[22] Filed: Sep. 27, 1989

[30] Foreign Application Priority Data

Oct. 15, 1988 [DE]  Fed. Rep. of Germany ....... 3835199

[51] Int. Cl.$^5$ .................... B01F 17/56; B07G 3/00; A61K 7/06
[52] U.S. Cl. ........................ 424/70; 252/351; 252/DIG. 1; 252/174.17; 536/4.1; 536/18.6
[58] Field of Search .............. 252/351, DIG. 1, 170, 252/174.17; 536/4.1, 18.6; 424/70

[56] References Cited

U.S. PATENT DOCUMENTS

| | | |
|---|---|---|
| 2,235,783 | 9/1939 | White ........................... 536/18.6 X |
| 2,715,121 | 8/1955 | Glen et al. ..................... 536/4.1 X |
| 2,974,134 | 3/1961 | Pollitzer ......................... 252/351 X |
| 3,340,239 | 9/1967 | Schweiger ..................... 536/4.1 X |
| 3,547,828 | 12/1970 | Mansfield et al. .............. 252/351 |
| 3,598,865 | 8/1971 | Lew ................................ 536/4.1 X |
| 4,565,647 | 1/1986 | Llanado ......................... 252/354 |
| 4,663,444 | 5/1987 | Egan .............................. 536/18.6 X |
| 4,704,453 | 11/1987 | Lorenz et al. ................... 536/18.6 |
| 4,753,885 | 6/1988 | Dietsche et al. ................ 435/255 X |
| 4,920,100 | 4/1990 | Lehmann et al. ............... 514/23 |

*Primary Examiner*—Richard D. Lovering
*Assistant Examiner*—Daniel S. Metzmaier
*Attorney, Agent, or Firm*—Oblon, Spivak, McClelland, Maier & Neustadt

[57] ABSTRACT

Substituted glucosides I $$(\text{Glu}_m-R^1)R_n^2 \qquad \text{I}$$

where Glu is a glucose unit, $R^1$ is $C_8-C_{18}$-alkyl held by an acetal bond, $R^2$ is $C_1-C_4$-alkyl or arylmethyl held by an ether bond, m is a mean value from 1 to 10 and n is a mean value from 0.1 to 2 m.

6 Claims, No Drawings

SUBSTITUTED GLUCOSIDES

The present invention relates to novel substituted glucosides of the general formula I $$(Glu_m-R^1)R_n^2 \qquad I$$

where Glu is a glucose unit, $R^1$ is $C_8$-$C_{18}$-alkyl held by an acetal bond, $R^2$ is $C_1$-$C_4$-alkyl or arylmethyl held by an ether bond, m is a mean value from 1 to 10 and n is a mean value from 0.1 m to 2 m.

The invention further relates to a process for the preparation of the glucoside I and of mixtures of these glucosides, and to their use as surfactants in detergents, cleansing agents and personal hygiene compositions.

DE-A 1,943,689 (1) discloses surface-active alkyl-oligosaccharides of the formula $$RO(C_6H_{10}O_5)_rH$$

where R is $C_{11}$-$C_{32}$-alkyl and r is not less than 2 but has a mean value of 3 or more. DE-B 1,905,523 (2) and DE-A 3,232,791 (3) relate to processes for the preparation of glucosides or glucoside mixtures, for example, in the case of (2), by acetalizing glucose with a monohydric $C_8$-$C_{25}$-alcohol in the presence of an acid. In a preferred embodiment the glucose is first reacted with a primary or secondary $C_3$-$C_5$-alcohol and then transacetalized to give the longer-chain alkylglucoside. (3) describes an improved process for the preparation of $C_3$-$C_5$-alkylglucosides in the presence of, for example, sodium perborate, which yields paler-colored products with a lower degree of condensation r.

The longer-chain alkylglucosides mentioned in (1) and (2) have hitherto been employed mainly as cleansing agents for industrial degreasing Hitherto, an obstacle to the more extensive use of these substances as surfactants or emulsifiers in detergents, cleansing agents or personal hygiene compositions was the excessively low hydrophobic character of the compounds, which resulted in too little lowering of the surface tension and too great foaming of formulations containing these substances.

It is an object of the present invention to remedy the said shortcomings.

We have found that this object is achieved by providing the substituted glucosides I defined at the outset.

The radical $R^1$ is a longer-chain alkyl of 8 to 18, preferably of 8 to 14, carbon atoms, linked to the 1-C atom of the glucose molecule by an acetal bond.

Examples of suitable radicals $R^1$ are octyl, nonyl, iso-nonyl, decyl, undecyl, lauryl, tridecyl, iso-tridecyl, myristyl, cetyl and stearyl.

$R^2$ is $C_1$-$C_4$-alkyl or arylmethyl, bonded to the 2-C, 3-C, 4-C and/or 6-C atom of the glucose molecule, in each case by an ether oxygen.

Examples of $R^2$ are especially methyl, ethyl and benzyl, but also propyl and butyl.

The degree of condensation m is from 1 to 10, preferably from 1 to 5. The occurrence of values of m greater than 1 is the result of the preparation of the precursors of I by acetalization of, for example, glucose in an acid medium, in which reaction condensation processes between the glucose molecules inescapably occur as a side reaction. As a rule, one is dealing with mixtures of the glucosides I, in which m is a mean value. These mixtures also contain small amounts of glucosides I with values of m greater than 10.

The degree of etherification n is from 0.1 m to 2 m, preferably from 0.1 m to m. As a rule, one is dealing with mixtures of the glucosides I with different degrees of etherification n, so that n is a mean value.

The novel substituted glucosides I or mixtures of these glucosides are advantageously prepared from the glucosides II $$Glu_m-R^1 \qquad II$$

by reaction with one or more compounds III $$R^2-X \qquad III$$

where X is a nucleophilic leaving group. This reaction takes place in aqueous alkaline solution, in a manner known per se.

The unsubstituted glucosides II serving as the precursor of I, and mixtures of glucosides II, as a rule have degrees of condensation m averaging from 1.5 to 3.

Per mole of II, from 0.1 m to 2 m moles, preferably from 0.1 m to m moles of III are employed. Suitable compounds III with a nucleophilic leaving group are methyl chloride, ethyl chloride, n-propyl chloride, iso-propyl chloride, n-butyl chloride, iso-butyl chloride, sec-butyl chloride, tert-butyl chloride, benzyl chloride and the corresponding bromine and iodine compounds, as well as dimethyl sulfate, diethyl sulfate, dipropyl sulfate and dibutyl sulfate. Mixtures of these alkylating agents may also be employed. The reaction of II with III is for example carried out in aqueous sodium hydroxide solution, potassium hydroxide solution or ammonia solution.

The novel glucosides I are used as surfactants, especially as nonionic surfactants or emulsifiers in detergents and cleansing agents, for example for cleaning processes in the industrial and domestic sector, such as washing of textiles or cleaning processes in the foodstuff sector, such as cleaning of drinks bottles. They are also used as emulsifiers in personal hygiene compositions such as skin creams or shampoos These detergents, cleansing agents and personal hygiene compositions contain from 20 to 70% by weight, preferably from 30 to 50% by weight, based on the total amount of the preparation, of the novel glucoside I or of mixtures of these.

In addition to their good performance characteristics, such as marked lowering of surface tension, low foaming and adequate wetting, the novel glucosides I are distinguished by good biodegradability. While the longer-chain alkylglucosides mentioned in (1) and (2) can undergo significant degradation in the presence of microorganisms, for example during storage, before they are ever used as cleansing agents, the novel glucosides do not suffer from this disadvantage; on the other hand the glucosides I, after having been used as intended, are degradable almost completely in sewage works.

A further advantage is the high purity of the glucosides I prepared by the process according to the invention, because unconverted III can be completely destroyed by heating the reaction mixture in alkaline solution, the alcohol thereby produced can easily be removed by distillation and the salt formed at the same time can frequently be readily removed by adding water, heating to above the cloud point, and separating off the lighter aqueous phase.

EXAMPLES

The starting compound and comparison product was a glucoside II prepared according to (2) and (3) from glucose and a $C_{10}$-$C_{12}$-alkanol distillation cut, the glucoside having a mean degree of condensation m of from 2.6 to 2.8.

EXAMPLE 1

700 g (0.90 mol) of glucoside II were dissolved in 300 g of water and 100 g of 50% strength by weight sodium hydroxide solution (corresponding to 1.25 mol of NaOH) were added, causing the temperature to rise to 44° C. At this temperature, 101.3 g (0.80 mol) of benzyl chloride were added dropwise over 1 hour, after which the reaction mixture was stirred for 6 hours at 60° C. After having added 500 g of water, 122 g of liquid were distilled off under a pressure of 130 mbar, the liquid consisting of water and small amounts of benzyl alcohol, which together form an azeotropic mixture. 1,580 g of an aqueous solution of the substituted glucoside I, having a solids content of 46.5% by weight, were obtained.

The product had a mean degree of aralkylation of n=0.9 and a mean degree of condensation m of from 2.6 to 2.8.

EXAMPLE 2

700 g (0.90 mol) of glucoside II were dissolved in 300 g of water and 152 g of 50% strength by weight sodium hydroxide solution (corresponding to 1.90 mol of NaOH) were added, causing the temperature to rise to 48° C. At this temperature, 152 g (1.20 mol) of benzyl chloride were added dropwise over 2 hours. The reaction mixture was then stirred for 11 hours at 80° C. 100 g of water were added and the mixture was heated to the boil. Azeotropic distillation served to separate off 100 g of liquid consisting of water and small amounts of benzyl alcohol. The phases were separated at 90°-95° C. The lower phase, which contained the substituted glucosides I, weighed 1,13 g and had a solids content of 50.3% by weight.

The product had a mean degree of aralkylation n of 1.3 and a mean degree of condensation m of from 2.6 to 2.8.

EXAMPLE 3

700 g (0.90 mol) of glucoside II were dissolved in 300 g of water and 200 g of 50% strength by weight sodium hydroxide solution (corresponding to 2.50 mol of NaOH) were added, causing the temperature to rise to 43° C. At this temperature, 203 g (1.60 mol) of benzyl chloride were added dropwise over 30 minutes. The reaction mixture was then stirred for 14 hours at 80° C. 2,000 g of water were added and the mixture was heated to the boil. Azeotropic distillation served to separate off 150 g of liquid consisting of water and small amounts of benzyl alcohol. The phases were separated at 90°-95° C. The lower phase, which contained the substituted glucosides I, weighed 1,160 g and had a solids content of 56.5% by weight.

This product had a mean degree of aralkylation n of 1.8 and a mean degree of condensation m of from 2.6 to 2.8.

To assess the performance characteristics of the glucoside I, the surface tension, the foaming power and the wetting power of aqueous preparations containing the novel glucoside mixtures of Examples 1 to 3 were investigated. The cloud point was also determined, to serve as a measure of the hydrophobic character of the surfaceactive substance.

The surface tension was determined in accordance with DIN 53914. In this, the force, in mN/m, needed to pull a horizontally suspended ring or stirrup from the liquid surface is measured.

The foaming power was determined according to DIN 53902 by measuring the foam volume in ml one minute after completing the generation of foam.

The wetting power was determined according to DIN 53901 by dipping a cotton fabric into the surfactant solution to be examined. The time after which the fabric loses its buoyancy attributable to the included air, and begins to sink, is measured. The shorter the time, the greater the wetting power.

The cloud point was measured according to DIN 53917. This test method originally related only to ethylene oxide adducts but is commonly also applied to other nonionic surfactants The cloud point is understood as the critical lower demixing temperature, in ° C, at which two phases form on lowering the temperature of a hot homogeneous mixture of the surfactant with a 25% strength by weight aqueous butyl diglycol solution The lower the cloud point, the greater the hydrophobic character of the surfactant.

The Table which follows shows the results obtained with the glucoside mixtures of Examples 1 to 3 and, for comparison, those obtained with the non-benzylated glucoside. An aqueous solution containing 0.1 g of anhydrous active ingredient per liter was used in each case to determine the surface tension. The wetting power was determined in an aqueous solution of 1.0 g of anhydrous active ingredient per liter.

TABLE

| | Surface tension at 20° C. [mN/m] | Foaming power [ml] | Wetting power at 25° C. [sec] | Cloud point [°C.] |
|---|---|---|---|---|
| Glucoside II (for comparison) | 36.0 | 550 | 75 | >100 |
| Example 1 | 31.6 | 210 | 160 | >100 |
| Example 2 | 30.2 | 60 | 270 | 85 |
| Example 3 | 31.2 | 50 | 105 | 63 |

We claim:
1. A substituted glucoside of the general formula I

$$(Glu_m\text{--}R^1)R_n^2 \qquad I$$

where Glu is a glucose unit, $R^1$ is $C_8$-$C_{18}$-alkyl bonded to the 1-C atom of a glucose unit by an acetal bond, $R^2$ is $C_1$-$C_4$-alkyl or arylmethyl bonded to the 2-C, 3-C, 4-C and/or 6-C atom of a glucose unit by an ether bond, m is a mean value from 1.5 to 3 and n is a mean value from 0.1 m to 2 m.

2. A substituted glucoside of the general formula I, as claimed in claim 1, where $R^2$ is methyl, ethyl or benzyl.

3. A substituted glucoside of the general formula I, as claimed in claim 1, where n is from 0.1 m to m.

4. A detergent, cleansing agent or personal hygiene composition which contains from 20 to 70% by weight, based on the total amount of the preparation, of a substituted glucoside I as claimed in claim 1, or of a mixture of such glucosides.

5. A method of washing, comprising applying a substituted glucoside I as claimed in claim 1 or a mixture of such glucosides to the surface of an object.

6. A method of practicing personal hygiene, comprising applying a substituted glucoside I as claimed in claim 1, or a mixture of such glucosides to skin or hair. substituted glucoside I as claimed in claim 1, or of a mixture of such glucosides

* * * * *